(12) United States Patent
Sugo

(10) Patent No.: US 8,591,428 B2
(45) Date of Patent: Nov. 26, 2013

(54) METHOD AND APPARATUS FOR MEASURING BLOOD VOLUME

(75) Inventor: Yoshihiro Sugo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 218 days.

(21) Appl. No.: 12/761,813

(22) Filed: Apr. 16, 2010

(65) Prior Publication Data

US 2010/0268101 A1    Oct. 21, 2010

(30) Foreign Application Priority Data

Apr. 17, 2009   (JP) ................................. 2009-100957

(51) Int. Cl.
*A61B 5/029*    (2006.01)
(52) U.S. Cl.
USPC ........................................................ 600/526
(58) Field of Classification Search
USPC .............. 607/23, 24; 600/513, 508, 481, 483, 600/323, 324
See application file for complete search history.

(56) References Cited

U.S. PATENT DOCUMENTS

| 5,241,966 | A | 9/1993 | Finkelstein et al. | |
| 5,743,268 | A * | 4/1998 | Kabal | 600/526 |
| 6,485,431 | B1 | 11/2002 | Campbell | |
| 2005/0222514 | A1 * | 10/2005 | Sugo et al. | 600/526 |
| 2008/0015451 | A1 * | 1/2008 | Hatib et al. | 600/481 |

FOREIGN PATENT DOCUMENTS

| JP | 2005-312947 A | 11/2005 |
| WO | 2008/019207 A2 | 2/2008 |

OTHER PUBLICATIONS

Smulyan, H., et al., "An Evolution of the Cardiac Index" American Heart Journal 1966, pp. 621-631, vol. 72.
European Search Report, issued Aug. 5, 2010 in counterpart European patent application No. 10160264.7.

* cited by examiner

*Primary Examiner* — George Evanisko
(74) *Attorney, Agent, or Firm* — Sughrue Mion, PLLC

(57) ABSTRACT

A method of measuring a blood volume, includes: reading individual specific information of a patient; estimating oxygen metabolism relating to a cardiac output of the patient; and acquiring the cardiac output based on the estimated oxygen metabolism.

11 Claims, 18 Drawing Sheets

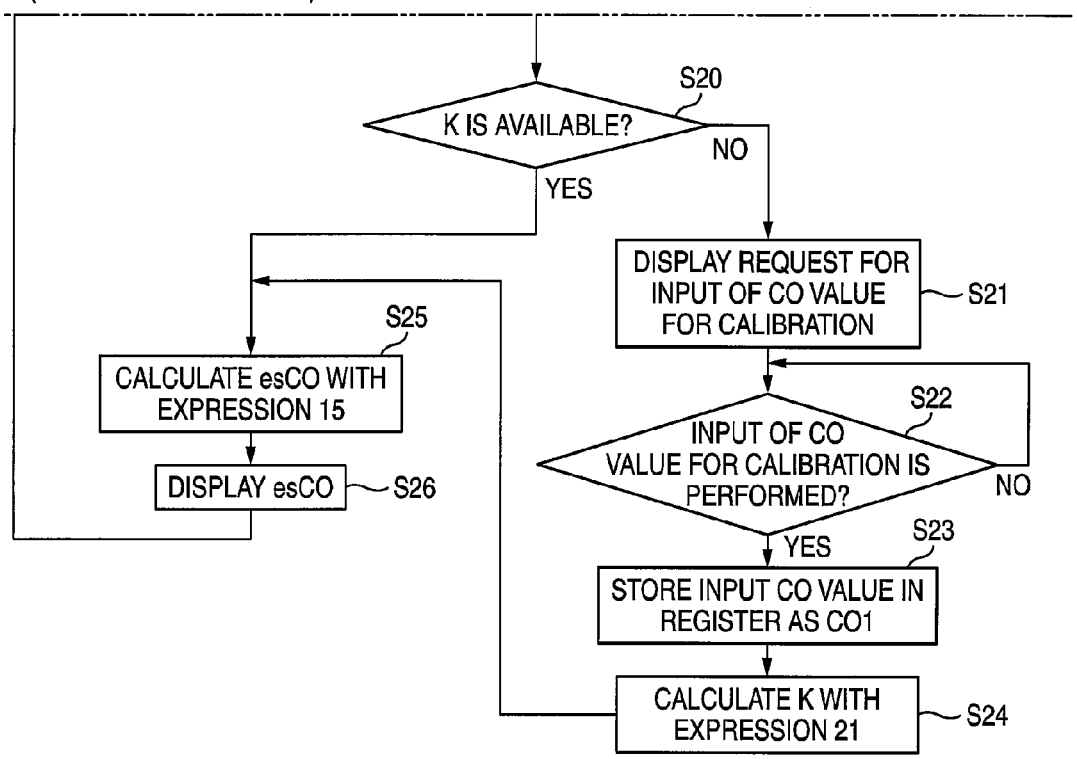
(FIG.17 CONTINUED)

METHOD AND APPARATUS FOR MEASURING BLOOD VOLUME

BACKGROUND OF THE INVENTION

The present invention relates to a method and an apparatus for measuring a blood volume which is ejected with each heartbeat.

In medical facilities, variation in the hemodynamics of a patient in an operating room, an intensive care unit, an emergency room, a dialysis treatment room, or the like needs to be monitored continuously as long as possible. Conventionally, monitoring of the variation in the hemodynamics of such a patient has been predominantly carried out by direct monitoring of a blood pressure. In a living body, a cardiac output and a vascular resistance are regulated such that the blood pressure of the centrum is limited within a predetermined range. In order to know the variation in the hemodynamics of the patient in an early stage, therefore, it is not enough to only monitor the blood pressure directly, and there is a need to know cause of change in the blood pressure when the change in blood pressure is observed. For this reason, there is a need to monitor a change of the cardiac output, in addition to monitoring the change in the blood pressure.

A method and apparatus for measuring a blood volume, and a biological signal monitoring apparatus are known in which variation in hemodynamics of the patient can be monitored always and continuously in an noninvasive manner, a skilled technique of a medical person such as insertion of a catheter is not required, less pain is experienced by the patient, there is no threat of infection because it is noninvasive, and the cost is low (see JP-A-2005-312947).

JP-A-2005-312947 discloses the principle of measuring the blood volume (cardiac output) which is ejected with each heartbeat in the following manner.

When a Windkessel model shown in FIG. 6 is used, the influx flow volume to the aorta during a systole, that is, the flow volume (SV−Qs) acquired by deducting the efflux flow volume to the periphery during a systole Qs from one stroke volume SV is represented by the aortic compliance C and the pulse pressure PP (see Expression 1). In this description, the term "pulse pressure" means a difference between the systolic blood pressure and the diastolic blood pressure.

$$SV - Qs = C \cdot PP \quad \text{(Exp. 1)}$$

The efflux flow volume to the periphery during a diastole Qd is equal to (SV−Qs).

Furthermore, Qs and Qd represent values acquired by dividing the systolic and diastolic arterial pressures V by the vascular resistance R and then multiplying by the systolic duration Ts and the diastolic duration Td, respectively. However, as it is estimated, for the matter of simplicity, that the flow volume values are proportional to Ts and Td, respectively, the values may be represented by Expression 2.

$$(Qd=)SV - Qs = SV \cdot Td/(Ts+Td) \quad \text{(Exp. 2)}$$

From Expressions 1 and 2, Expression 3 is acquired as follows.

$$SV \cdot Td/(Ts+Td) = C \cdot PP$$

$$SV = C \cdot PP \cdot (1 + Ts/Td) \quad \text{(Exp. 3)}$$

Here, when it is assumed that C and Ts/Td remain constant during the measurement period, and $C \cdot (1+Ts/Td)$ is represented by K, the following is acquired.

$$SV = K \cdot PP \quad \text{(Exp. 4)}$$

$$PP = SV/K \quad \text{(Exp. 5)}$$

In this way, according to the Windkessel model, the pulse pressure is proportional to SV.

In practice, actually measured pulse pressure PP1 is configured by the pulse pressure PP2 (although this is represented by PP in Expression 5, hereinafter it will be represented by PP2), and the augmentation PP3 in the pulse pressure observed upon administration of a vasoconstrictor or the like, as in following Expression 6.

$$PP1 = PP2 + PP3 \quad \text{(Exp. 6)}$$

In a case where PP3 is not observed, Expressions 4 and 6 lead to:

$$SV = K \cdot PP1 \quad \text{(Exp. 7)}$$

Therefore, SV can be directly measured from the measurement of blood pressure. However, since PP1 already includes PP3 in the administration of a vasoconstrictor or the like, SV would be overestimated.

This has been a problem when SV is calculated from the blood pressure.

With regard to the accuracy in measurement of an apparatus which enables calculation of the stroke volume as well as the cardiac output from the waveform of the arterial pressure measured invasively, the following is reported: "For a patient admitted to the ICU (intensive care unit) after a surgery, when the vascular resistance changed by about 60% upon administration of a vasoconstrictor phenylephrine, a remarkably large bias was observed between the measurements by the apparatus described above and the measurements by the cardiac output computer operating in the thermodilution mode used as the standard method, the values of the former being greater than those of the latter. In that case, there is accordingly a need for re-calibration by the blood volume flowmeter operating in the thermodilution mode." Further, in the administration of a vasoconstrictor, it is known that, in the administration of a vasoconstrictor or the like, the pulse pressure increases by influence of a reflected wave from the periphery, and PP3 corresponds to this augmentation.

In electrocardiography, the pulse wave propagation time (hereinafter, referred to as PWTT), which corresponds to a time taken until the reach of the propagated pulse wave to the SpO$_2$ at the periphery, is configured by following Expression 8.

$$PWTT = PEP + PWTT1 + PWTT2 \quad \text{(Exp. 8)}$$

Here, as shown in FIG. 11, PEP is the pre-ejection period of the heart, which is the duration from the initiation of electric stimulation of the heart to the opening of the aortic valve. PWTT1 is a time taken for the pulse wave to be propagated from its generation in the aorta after the opening of the aortic valve to an artery at the periphery where typically blood pressure measurement is conducted invasively. PWTT2 is a time taken for the pulse wave to be further propagated from the artery at the periphery to a peripheral blood vessel where photoplethysmogram is measured.

The duration of (PEP+PWTT1) from the R wave of electrocardiogram (ECG) to the onset of rising in the pulse wave at the femoral artery was measured using ten adult dogs, and measured the relationship between the duration of (PEP+PWTT1) and the pulse pressure with administration of a vasoconstrictor in the respective cases under conditions such as, administration of a vasodilator, increase of the myocardial contractility, attenuation of myocardiac contractility, and blood removal. In this way, it was found good correlation between the pulse pressure PP1 and the duration of (PEP+PWTT1).

FIG. 7 is a view showing the representative relationship between the PWTT and the pulse pressure PP.

Therefore, the relationship between the pulse pressure PP1 and (PEP+PWTT1) can be represented by following Expression 9.

$$PEP+PWTT1 = a \cdot PP1 + b \quad \text{(Exp. 9)}$$

Further, the relationship between PWTT2 and PP1 is represented by following Expression 10.

$$PWTT2 = c \cdot PP1 + d + e \quad \text{(Exp. 10)}$$

Since it was discovered that, in a case where PP3 appears with the use of a vasoconstrictor, PWTT2 tends to be prolonged as compared to cases under other conditions, a portion corresponding to this prolongation is represented by "e" (where, a, b, c, d are constants, e is not limited to a constant).

Substituting Expressions 9 and 10 for Expression 8, Equation 11 is acquired as follows.

$$PWTT = (a \cdot PP1 + b) + (c \cdot PP1 + d + e)$$

$$PP1 = (PWTT - b - d - e)/(a + c) \quad \text{(Exp. 11)}$$

As PP2 in Expression 6 is replaced with the right-hand side of Expression 5, following Expression 12 is acquired.

$$PP1 = SV/K + PP3 \quad \text{(Exp. 12)}$$

From Expressions 11 and 12, the following Expression 13 is acquired.

$$PWTT/(a+c) - (b+d)/(a+c) = SV/K + PP3 + e/(a+c)$$

$$SV = K \cdot (PWTT/(a+c) - (b+d)/(a+c)) - K \cdot (PP3 + e/(a+c)) \quad \text{(Exp. 13)}$$

As described above, it has been experimentally found that PWTT2 tends to be prolonged when PP3 is observed upon use of a vasoconstrictor or the like. FIG. 10 shows this relationship.

When phenylephrine is administered, PP3 is observed and accordingly PP1 is increased, as shown in FIG. 10. However, the relationship between PWTT2 and PP1 which may be observed in cases of blood removal or administration of pentobarbital is no longer observed with the administration of phenylephrine, and PWTT2 shows a tendency to be prolonged.

Therefore, it has been experimentally discovered that, as shown in FIG. 9, there is maintained a negative correlation between SV and PWTT even upon administration of phenylephrine, which may be still observed under different conditions, and thus the second term $(K \cdot (PP3 + e/(a+c)))$ in the right-hand side of Expression 13 may be substantially ignored.

Here, taking $1/(a+c) = \alpha$ and $-(b+d)/(a+c) = \beta$, following Expression 14 is acquired.

$$SV = K \cdot (\alpha \cdot PWTT + \beta) \quad \text{(Exp. 14)}$$

where $\alpha$ and $\beta$ are empirically acquired coefficients that are inherent to the patient.

Moreover, the cardiac output can be calculated from following Expression 15.

$$esCO = K \cdot (\alpha \cdot PWTT + \beta) \cdot HR \quad \text{(Exp. 15)}$$

wherein esCO [L/min] is the cardiac output, and K is an empirically acquired constant which is inherent to the patient. HR is a heart rate of the patient.

In addition, Expression 15 may be substituted in the same way as in Expression 16.

$$esCO = (\alpha K \cdot PWTT + \beta K) \cdot HR \quad \text{(Exp. 16)}$$

where $\alpha K$ and $\beta K$ are empirically acquired coefficients which are inherent to the patient.

When SV and esCO are calculated using PWTT as expressed in Expressions 14, 15 and 16, as shown in FIG. 9, there is maintained correlation between SV and PWTT which may be observed under different conditions, even in a case of an augmentation in the pulse pressure associated with the use of a vasoconstrictor, as shown in FIG. 8, and thus problems that can be seen with the conventional practice of calculating SV by blood pressure may be solved.

Naturally, there is no risk of overestimation of CO.

FIGS. 8 and 9 show relationships between SV and PP1 and between SV and PWTT as measured during vascular constriction, blood removal, and cardiac suppression in an animal test.

Incidentally, there occurred an increase in the vascular resistance by more than 60% upon administration of phenylephrine.

Next, an example of a biological signal monitoring apparatus to which the conventional method of measuring a blood volume is applied will be described in detail with reference to the drawings.

FIG. 12 is a block diagram illustrating the configuration of the example of the conventional biological signal monitoring apparatus, and FIG. 13 is a diagram illustrating an example of the manner of a measurement in which the conventional biological signal monitoring apparatus. FIG. 11 is a view showing waveforms of measured pulse waves.

A systolic/diastolic blood pressure measuring unit 20 includes a cuff 25, a compressing pump 27, a pressure sensor 28, a cuff pressure detector 29, an A/D converter 22, and the like, as shown in FIG. 12.

Specifically, the cuff 25 is attached to an upper arm of a patient for measurement, as shown in FIG. 13. In the cuff 25, the interior is opened or closed with respect to the atmosphere by an exhaust valve 26 installed in a body 10 of the biological signal monitoring apparatus. Air is supplied to the cuff 25 by the compressing pump 27 installed in the body 10 of the biological signal monitoring apparatus. The pressure sensor 28 (cuff pulse wave sensor) is mounted in the body 10 of the biological signal monitoring apparatus, and an output of the sensor is detected by the cuff pressure detector 29.

An output of the cuff pressure detector 29 is converted into a digital signal by the A/D converter 22, and input to a cardiac output calculating unit 40 (in FIG. 13, the cuff pressure detector 29, the A/D converter 22, and the cardiac output calculating unit 40 are included in the body 10 of the biological signal monitoring apparatus).

In FIG. 11, (a) shows an electrocardiogram waveform, and an aortic pressure wave immediately after the ejection from the heart has a waveform shown in (b) of FIG. 11. Further, waveforms of an arterial pressure wave at the periphery and a peripheral pulse wave are acquired as shown (c) and (d) of FIG. 11.

As shown in FIG. 12, a pulse wave propagation time measuring unit 30 includes a time interval detection reference point measuring unit 31, an A/D converter 32, a photoplethysmogram sensor 33, a pulse wave detector 34, an A/D converter 35, etc.

The time interval detection reference point measuring unit 31 is used for detecting a point of time when an R wave is generated on an electrocardiogram, and an output thereof is converted into a digital signal by the A/D converter 32, and then input to the cardiac output calculating unit 40. Specifically, the time interval detection reference point measuring unit 31 is configured by ECG electrodes 31a (electrocardiogram measuring unit) which are attached to the chest of the subject, as illustrated in FIG. 13. Measurement data is transmitted from a measurement data transmitter 50 which is electrically connected to the ECG electrodes 31a, to the body 10 of the biological signal monitoring apparatus in a wireless manner. The transmitted measurement data is converted into a digital signal by the A/D converter 32 in the body 10 of the biological signal monitoring apparatus, and then input to the cardiac output calculating unit 40. In this way, the ECG waveform as shown in (a) of FIG. 11 is acquired.

Meanwhile, the photoplethysmogram sensor 33 is intended to be attached to a peripheral part, such as a finger, of the patient, as shown in FIG. 13, and to be used in acquiring the pulse wave propagation time, for example, by performing SpO2 measurement. The photoplethysmogram sensor 33 is electrically connected to the measurement data transmitter 50, and the measurement data transmitter 50 transmits the measurement data to the main body 10 of the biological signal monitoring apparatus in a wireless manner. When the measurement data is sent to the pulse wave detector 34 in the main body 10 of the biological signal monitoring apparatus, the pulse wave (photoplethysmogram) at the attachment location of the patient is detected. The output of the pulse wave detector 34 is converted into a digital signal by the A/D converter 35 and then input to the cardiac output calculating unit 40. As such, a waveform of the photoplethysmogram (a waveform at the periphery) such as shown in (d) of FIG. 11 is acquired.

Next, a calculation process of acquiring esCO from the Expressions 15 and 16 will be described with reference to FIGS. 14 to 17.

First, the procedure in which βK is acquired by calibration using a default value of αK and then esCO is calculated will be described with reference to FIG. 14.

Reading of the default value of αK is carried out (Step S1). PWTT and HR are acquired (Step S2). Next, it is determined whether βK is available or not (Step S3). If the determination in Step S3 is NO, then a request for input of cardiac output (CO) value for calibration is displayed (Step S4). It is determined whether the CO value for calibration has been input or not (Step S5). If the determination in Step S5 is YES, the input CO value, and the acquired PWTT and HR are stored in a register as CO1, PWTT1, and HR1, respectively (Step S6). βK is acquired from following Expression 17 (Step S7).

$$\beta K = CO1/HR1 - \alpha K \cdot PWTT1. \quad \text{(Exp. 17)}$$

Calculation of acquiring esCO from the Expression 16 is carried out by using the acquired βK (Step S8). If the determination in Step S3 is YES, likewise, calculation of acquiring esCO from the Expression 16 is carried out (Step S8). The esCO acquired in the calculation is displayed (Step S9).

The above procedure is repeated as required.

Next, the procedure in which αK and βK are acquired by calibration and then esCO is calculated will be described with reference to FIG. 15. Reading of the default value of αK is carried out (Step S1). PWTT and HR are acquired (Step S2). Next, it is determined whether βK is available or not (Step S3). If the determination in Step S3 is NO, then a request for input of CO value for calibration is displayed (Step S4). It is determined whether the CO value for calibration has been input or not (Step S5). If the determination in Step S5 is YES, the input CO value, and the acquired PWTT and HR are stored in a register as CO1, PWTT1, and HR1, respectively (Step S6). βK is acquired from the Expression 17 (Step S7). Calculation of acquiring esCO from the Expression 16 is carried out by using the acquired βK (Step S8). If the determination in Step S3 is YES, it is determined whether re-calibration for αK should be carried out or not (Step S10). If the determination in Step S10 is NO, likewise, calculation of acquiring esCO from the Expression 16 is carried out (Step S8). If the determination in Step S10 is YES, a request for input of the CO value for calibration is displayed (Step S11). It is determined whether the CO value for calibration has been input or not (Step S12). If the determination in Step S12 is YES, the input CO value, and the acquired PWTT and HR are stored in the register as CO2, PWTT2, and HR2, respectively (Step S13). αK and βK are calculated from following Expressions 18 and 19 (Step S14).

$$CO1 = (\alpha K \cdot PWTT1 + \beta K) \cdot HR1 \quad \text{(Exp. 18)}$$

$$CO2 = (\alpha K \cdot PWTT2 + \beta K) \cdot HR2 \quad \text{(Exp. 19)}$$

Calculation of acquiring esCO from the Expression 16 is carried out by using the acquired αK and βK (Step S8). If the determination in Step S10 is NO, calculation of acquiring esCO from the Expression 16 is carried out (Step S8). The esCO acquire in the calculation is displayed (Step S9).

The above procedure is repeated as required.

Then, the procedure in which α is the default value, β and K are acquired by calibration, and then esCO is calculated will be described with reference to FIG. 16. The calibration of β is carried out when the pulse pressure is not augmented by administration of a vasoconstrictor or the like.

Reading of the default value of α is carried out (Step S1). PWTT and HR are acquired (Step S2). Next, it is determined whether β is available or not (Step S15). If the determination in Step S15 is NO, then a request for measurement of blood pressure for calibration is displayed (Step S16). It is determined whether measurement of the blood pressure for calibration has been conducted or not (Step S17). If the determination in Step S17 is YES, the measured PP value, and the acquired PWTT and HR are stored in the register as PP1, PWTT1, and HR1, respectively (Step S18). β is calculated from following Expression 20 (Step s19).

$$\beta = PP1 - \alpha \cdot PWTT1 \quad \text{(Exp. 20)}$$

If the determination in Step S15 is YES, or after β is calculated in Step S19, it is determined whether K is available or not (Step S20). If the determination in Step S20 is NO, a request for input of CO value for calibration is displayed (Step S21). It is determined whether the CO value for calibration has been input or not (Step S22). If the determination in Step S22 is YES, the input CO value is stored in the register as CO1 (Step S23). K is calculated from following Expression 21 (Step S24).

$$K = CO1/\{(\alpha \cdot PWTT1 + \beta) \cdot HR1\} \quad \text{(Exp. 21)}$$

If the determination in Step S20 is YES, or after K is calculated in Step S24, esCO is calculated from the Expression 15 (Step S25). The esCO acquired in the calculation is displayed (Step S26).

The above procedure is repeated as required.

Then, the procedure in which α, β, and K are acquired by calibration, and then esCO is calculated will be described with reference to FIG. 17. The calibration of α and β is carried out when the pulse pressure is not augmented by administration of a vasoconstrictor or the like.

Reading of the default value of α is carried out (Step S1). PWTT and HR are acquired (Step S2). Next, it is determined whether β is available or not (Step S15). If the determination in Step S15 is NO, then a request for measurement of blood pressure for calibration is displayed (Step S16). It is determined whether measurement of the blood pressure for calibration has been conducted or not (Step S17). If the determination in Step S17 is YES, the measured PP value, and the acquired PWTT and HR are stored in the register as PP1, PWTT1, and HR1, respectively (Step S18). β is calculated from the Expression 20 (Step S19). If the determination in Step S15 is YES, it is determined whether re-calibration for α should be carried out or not (Step S27). If the determination in Step S27 is YES, then a request for measurement of blood pressure for calibration is displayed (Step S28). It is determined whether measurement of the blood pressure for calibration has been conducted or not (Step S29). If the determination in Step S29 is YES, the measured PP value, and the acquired PWTT and HR are stored in the register as PP2, PWTT2, and HR2, respectively (Step S30). α and β are calculated from following Expressions 22 and 23.

$$PP1=\alpha \cdot PWTT1+\beta \quad \text{(Exp. 22)}$$

$$PP2=\alpha \cdot PWTT2+\beta \quad \text{(Exp. 23)}$$

If the determination in Step S27 is NO and the processes of Steps S19 and S31, it is determined whether K is available or not (Step S20). If the determination in Step S20 is NO, a request for input of CO value for calibration is displayed (Step S21). It is determined whether the CO value for calibration has been input or not (Step S22). If the determination in Step S22 is YES, the input CO value is stored in the register as CO1 (Step S23). K is calculated from the Expression 21 (Step S24). If the determination in Step S20 is YES, or after K is calculated in Step S24, esCO is calculated from the Expression 15 (Step S25). The esCO acquired in the calculation is displayed (Step S26).

The above procedure is repeated as required.

Alternatively, the measurement of blood pressure for calibration may not be performed, and a blood pressure value which is measured by another sphygmomanometer may be key-input. Furthermore, the peripheral pulse wave may include also that indicative of a volumetric change in addition to the SpO2 pulse wave.

According to JP-A-2005-312947, a method and apparatus for measuring a blood volume, and a biological signal monitoring apparatus can be realized in which variation in hemodynamics of the patient can be monitored always and continuously in an noninvasive manner, a skilled technique of a medical person such as insertion of a catheter is not required, less pain is experienced by the patient, there is no threat of infection because it is noninvasive, and the cost is low.

Also in the above-described method and apparatus for measuring a blood volume, and biological signal monitoring apparatus which are disclosed in JP-A-2005-312947, although improvements are made as compared with the conventional art, calibration in which the CO value for calibration is input substantially at least one time is necessary. In view of the requirement of a skilled technique of a medical person, and the high degree of invasion of the patient, therefore, the monitoring cannot be performed in an easy and continuous manner. Therefore, there is a problem in that the method is difficult to monitor always and continuously variation in hemodynamics of the patient.

SUMMARY

It is therefore an object of the invention to provide a method and an apparatus for measuring a blood volume in which a cardiac output of a patient is acquired by inputting individual specific information relating to oxygen metabolism of the patient without inputting a CO value for calibration, and the acquired cardiac output is used in calibration.

In order to achieve the object, according to the invention, there is provided a method of measuring a blood volume, the method comprising:

reading individual specific information of a patient;

estimating oxygen metabolism relating to a cardiac output of the patient; and acquiring the cardiac output based on the estimated oxygen metabolism.

The individual specific information may include at least a body surface area, age, sexuality, blood pressure, and heart rate of the patient.

The individual specific information may further include one of a pulse wave velocity and a pulse wave propagation time.

The cardiac output may be acquired by using an expression of $CO=a+b\cdot Sex+c\cdot Age+d\cdot BSA+e\cdot PWTT+f\cdot HR\cdot PP$, where CO is the cardiac output; Sex is the sexuality of the patient, when the patient is male, Sex=1, and when the patient is female, Sex=−1; Age is the age of the patient; BSA is the body surface area of the patient; PWTT is a pulse wave propagation time; HR is the heart rate of the patient; PP is a pulse pressure of the patient; and a, b, c, d, e, and f are coefficients inherent to the patient.

The cardiac output may be acquired by using an expression of $$CO=HR\cdot(a1+b1\cdot Sex+c1\cdot Age+d1\cdot BSA+e1\cdot HR_0\cdot PP_0)(\alpha\cdot PWTT+\beta)/PP_0\cdot HR_0$$

where CO is the cardiac output; Sex is the sexuality of the patient, when the patient is male, Sex=1, and when the patient is female, Sex=−1; Age is the age of the patient; BSA is the body surface area of the patient; PWTT is a pulse wave propagation time; HR is the heart rate of the patient; $HR_0$ is HR input at a timing of calibration; $PP_0$ is a pulse pressure PP input at the timing of calibration; α and β are coefficients inherent to the patient; and a1, b1, c1, d1, and e1 are constants.

The constants a1, b1, c1, d1, and e1 may be previously acquired by multiple linear regression analysis from individual specific information and actual CO values of a plurality of subjects.

The cardiac output may be acquired by using an expression of $$CO=HR\cdot(a2+b2\cdot Sex+c2\cdot Age+d2\cdot BSA+e2\cdot HR_0\cdot PP_0+f2\cdot PWTT_0)(\alpha\cdot PWTT+\beta)/PP_0\cdot HR_0$$

where CO is the cardiac output; Sex is the sexuality of the patient, when the patient is male, Sex=1, and when the patient is female, Sex=−1; Age is the age of the patient; BSA is the body surface area of the patient; PWTT is a pulse wave propagation time; HR is the heart rate of the patient; $HR_0$ is HR input at a timing of calibration; $PP_0$ is a pulse pressure PP input at the timing of calibration; $PWTT_0$ is PWTT input at the timing of calibration; α and β are coefficients inherent to the patient; and a2, b2, c2, d2, e2, and f2 are constants.

The constants a2, b2, c2, d2, e2, and f2 may be previously acquired by multiple linear regression analysis from individual specific information and actual CO values of a plurality of subjects.

According to the invention, there is provided a computer-readable recording medium in which a computer program causing a blood measuring apparatus to execute the method according to claim 1 is recorded.

In order to achieve the object, according to the invention, there is also provided an apparatus for measuring a blood volume, the apparatus comprising:

a first receiver receiving an input of individual specific information of a patient; and a controlling unit estimating oxygen metabolism relating to a cardiac output of the patient, and acquiring the cardiac output based on the estimated oxygen metabolism.

The apparatus may further comprise a second receiver receiving a timing of calibration is input.

The apparatus may further comprise: a time interval detection reference point measuring unit; a pulse wave detecting unit; a heart rate calculating unit which calculate a heart rate based on output from the time interval detection reference point measuring unit or the pulse wave detecting unit; an inputting unit through which at least an age, sexuality, and BSA of the patient are input; and a blood pressure inputting or blood pressure measuring unit.

The time interval detection reference point measuring unit may be an electrocardiogram measuring unit.

DETAILED DESCRIPTION OF EMBODIMENTS

Figure 1:
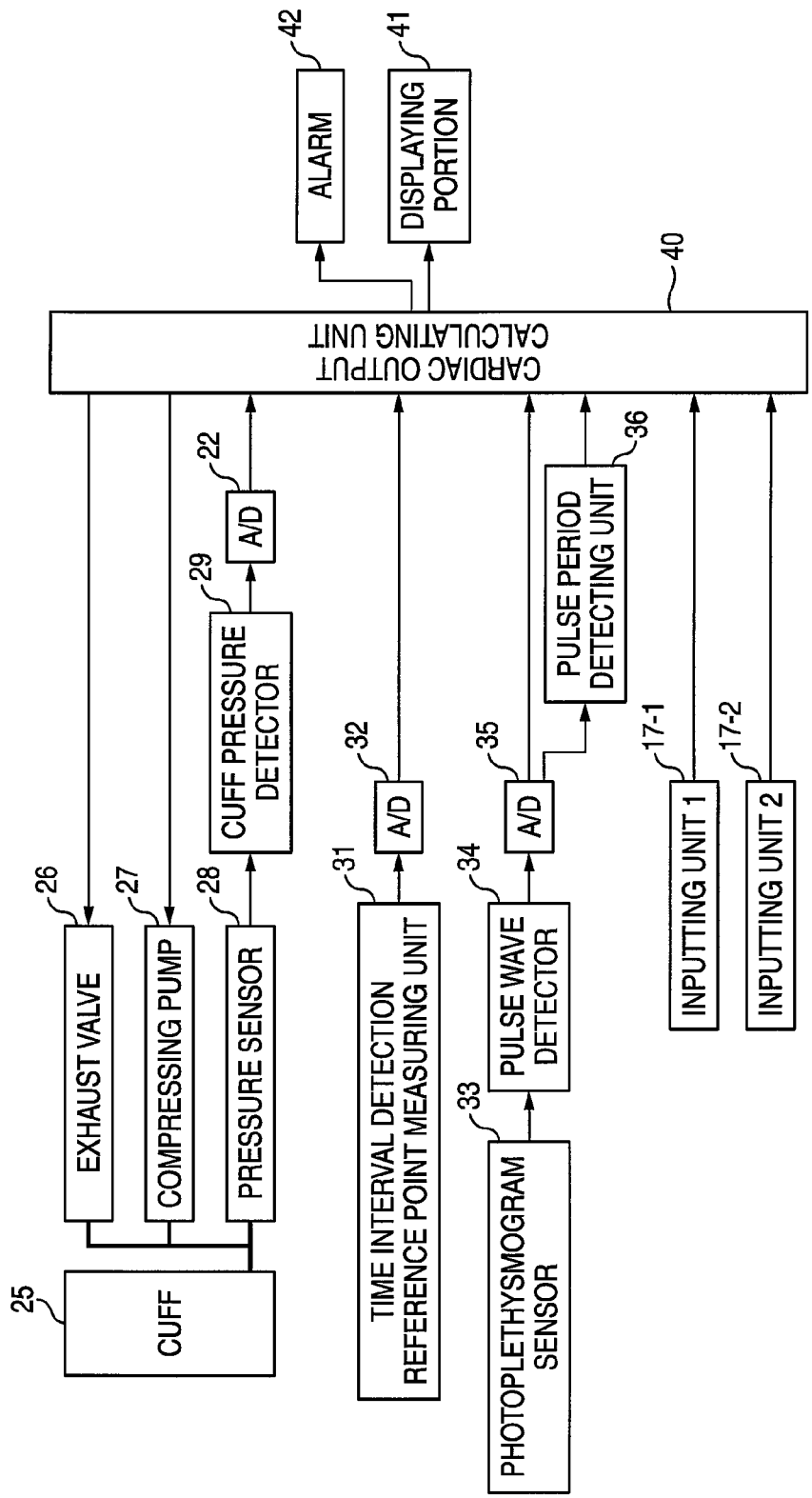
FIG. 1 is a block diagram illustrating the configuration of a biological signal monitoring apparatus of the present invention.

First, individual specific information which relates to a cardiac output used in the present invention, and which relates to oxygen metabolism of a patient will be described. In the cardiac output, a stroke volume of blood containing oxygen from the heart is controlled in accordance with oxygen metabolism of a living body. Although information relating to the oxygen metabolism of the living body does not directly reflect the cardiac output, therefore, the information relates the cardiac output.

In the invention, the individual specific information which relates to the oxygen metabolism of the patient, includes at least, the body surface area, the age, the sex, the blood pressure, and the heart rate. Also the pulse wave propagation time may be used.

It is seemed that the cardiac output is governed mainly by the oxygen consumption or rate of metabolism of the human body, and the rate of metabolism is best corrected by the body surface area. The rate of metabolism of the human body depends on the age, is maximum in childhood, and further decreases as the age is more increased. The cardiac output and the cardiac index are inversely correlated with the age. The cardiac index is a value which is acquired by dividing the cardiac output by the body surface area. A female is lower in basal rate of metabolism than a male. Usually, the myocardial oxygen consumption uses a product (i.e., a double product) of the heart rate and the systolic blood pressure, as an index. As the movement intensity is more increased, the mean blood pressure is gradually increased. Particularly, the systolic blood pressure is remarkably raised, and the diastolic blood pressure is raised by only a low degree. Therefore, the myocardial oxygen consumption can be the that it is equal to a product of the heart rate and the difference between the systolic blood pressure and the diastolic blood pressure, or the pulse pressure and the heart rate. The pulse wave velocity is the reciprocal of the pulse wave propagation time. The pulse wave velocity is indicated in the following manner.

Pulse wave velocity=3.57/(Square root of Percentage of increase of capacity with respect to increase of blood pressure)

When a blood vessel has a high extensibility, the percentage of increase of the capacity with respect to increase of the blood pressure is large, and the pulse wave velocity is reduced. In the case where the same blood pressure change occurs, namely, the degree of change of the cardiac output is reflected in the pulse wave velocity. In other words, a change of the cardiac output is reflected in the pulse wave propagation time. Furthermore, it is known that the pulse wave velocity changes with aging.

In the calculation of the cardiac output for calibration in the invention, the coefficients and the constant are acquired for a plurality of subjects by using the technique of multiple linear regression analysis in statistical analysis.

CALC-CO=$a+b\cdot$Sex+$c\cdot$Age+$d\cdot$BSA+$e\cdot$PWTT+ $f\cdot$HR$\cdot$PP where a=1.18, b=0.061, c=−0.0267, d=3.26, e=−0.011, and f=0.000487, Sex: Male=1; and Female=−1.

Next, an embodiment of a biological signal monitoring apparatus to which the method of measuring a blood volume according to the invention is applied will be described with reference to the drawings. FIG. 1 is a block diagram illustrating the configuration of the embodiment of the biological signal monitoring apparatus of the invention.

A systolic/diastolic blood pressure measuring unit includes the cuff 25, the compressing pump 27, the pressure sensor 28, the cuff pressure detector 29, the A/D converter 22, and the like, as shown in FIG. 1.

Specifically, the cuff 25 is attached to an upper arm of the patient for measurement. In the cuff 25, the interior is opened or closed with respect to the atmosphere by the exhaust valve 26 installed in the body 10 of the biological signal monitoring apparatus. Air is supplied to the cuff 25 by the compressing pump 27 installed in the body 10 of the biological signal monitoring apparatus. The pressure sensor 28 (cuff pulse wave sensor) is mounted in the body 10 of the biological signal monitoring apparatus, and an output of the sensor is detected by the cuff pressure detector 29. An output of the cuff pressure detector 29 is converted into a digital signal by the A/D converter 22, and input to the cardiac output calculating unit 40.

A pulse wave propagation time measuring unit includes the time interval detection reference point measuring unit 31, the A/D converter 32, the photoplethysmogram sensor 33, the pulse wave detector 34, the A/D converter 35, etc.

The time interval detection reference point measuring unit 31 is used for detecting a point of time when an R wave is generated on an electrocardiogram, and the output of the detecting portion is converted into a digital signal by the A/D converter 32, and then input to the cardiac output calculating unit 40. The time interval detection reference point measuring unit 31 is configured by the ECG electrodes 31a (electrocardiogram measuring unit) which are attached to the chest of the subject. Measurement data is transmitted from the measurement data transmitter 50 which is electrically connected to the ECG electrodes 31a, to the body 10 of the biological signal monitoring apparatus in a wireless manner. The transmitted measurement data is converted into a digital signal by the A/D converter 32 in the body 10 of the biological signal monitoring apparatus, and then input to the cardiac output calculating unit 40. In this way, the ECG waveform is acquired.

Meanwhile, the photoplethysmogram sensor 33 is intended to be attached to a peripheral part, such as a finger, of the patient, and to be used in acquiring the pulse wave propagation time, for example, by performing SpO2 measurement. The measurement data of the photoplethysmogram sensor 33 is transmitted to the pulse wave detector 34 in the body 10 of the biological signal monitoring apparatus in a wireless manner, whereby the pulse wave (photoplethysmogram) at the attachment location of the patient is detected.

The reference numeral 17-1 denotes an inputting unit 1 which is means for inputting the body surface area, age, and sexuality constituting the individual specific information, and that relates to oxygen metabolism of the patient.

The reference numeral 17-2 denotes another inputting unit 2 which is means for inputting a timing of calibration.

Next, calibration of $\alpha$, $\beta$, and K in a calculation process of acquiring esCO from the Expression 16 will be described with reference to FIGS. 2 to 5.

In advance of description of flowcharts, the technical meanings of K, $\alpha$, and $\beta$ will be described.

From the Expression 4, the following expression is acquired.

$$K = SV/PP$$

Therefore, K is the reciprocal of the ratio of SV (one stroke volume of the heart) to PP (pulse pressure). In a person in which the blood vessel is more rigid, K is smaller. When K is acquired, it is possible to correct individual differences of the relationship between one stroke volume of the heart and the pulse pressure.

From the expression, $PP = \alpha \cdot PWTT + \beta$, the following expression is acquired.

$$\alpha = \Delta PP/\Delta PWTT$$

Therefore, $\alpha$ is the ratio of the variation of PP to that of PWTT. In a person in which the blood vessel is more rigid, $\alpha$ is larger. When $\alpha$ is acquired, it is possible to correct individual differences of the relationship between the variations of PWTT and PP due to the rigidity of a blood vessel. Although the degree of $\alpha$ is different depending on the kind of the animal, there arises no serious problem even when it is deemed to be constant in the same kind.

From the expression, $PP = \alpha \cdot PWTT + \beta$, the following expression is acquired.

$$\beta = PP - \alpha \cdot PWTT$$

The length and rigidity of a blood vessel are reflected in $\beta$. When $\beta$ is acquired, it is possible to correct individual differences of the length and rigidity of a blood vessel.

From the Expression 14, the following expression is acquired.

$$K\alpha = \Delta SV/\Delta PWTT$$

Therefore, K$\alpha$ is the reciprocal of the ratio of the variation of PWTT to that of SV. In a person in which the blood vessel is more rigid, K is smaller, and in contrast $\alpha$ is larger. Therefore, K$\alpha$ is a coefficient in which individual differences due to the rigidity of a blood vessel are absorbed. When K$\alpha$ is acquired, it is possible to correct individual differences of the relationship between the variations of SV and PWTT.

From the Expression 14, the following expression is acquired.

$$K\beta = SV - K \cdot \alpha \cdot PWTT$$

The length and rigidity of a blood vessel are reflected in K$\beta$. When K$\beta$ is acquired, it is possible to correct individual differences of the length and rigidity of a blood vessel.

Figure 2:
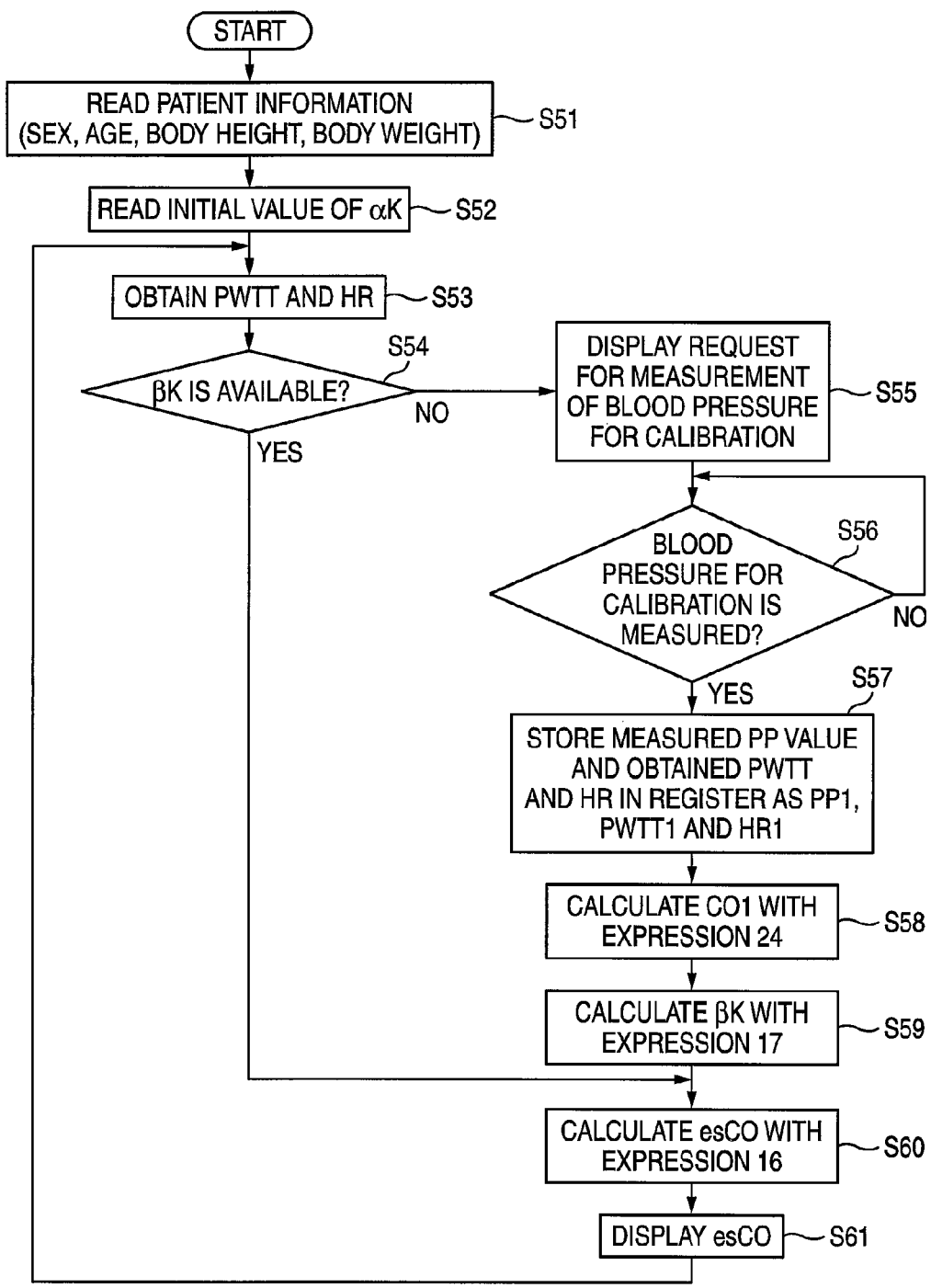
FIG. 2 is a flowchart showing a procedure in the invention in which a default value of $\alpha K$ is used, $\beta K$ is calibrated, and esCO is calculated.

First, the procedure in which $\beta$K is acquired by calibration using a default value of $\alpha$K and then esCO is calculated will be described with reference to FIG. 2.

First, reading of specific information (sex, age, body height, and body weight) of a patient is carried out (Step S51). Reading of the default value of $\alpha$K is carried out (Step S52). PWTT and HR are acquired (Step S53). Next, it is determined whether $\beta$K is available or not (Step S54). If the determination in Step S54 is NO, then a request for measurement of blood pressure for calibration is displayed (Step S55). It is determined whether measurement of the blood pressure for calibration has been conducted or not (Step S56). If the determination in Step S56 is YES, the measured value of the blood pressure PP, and PWTT and HR which are acquired in Step S53 are stored in a register as PP1, PWTT1, and HR1, respectively (Step S57). CO1 is calculated by using following Expression 24 (Step S58).

$$CO1 = a + b \cdot Sex + c \cdot Age + d \cdot BSA + e \cdot PWTT1 + f \cdot HR1 \cdot PP1 \quad (Exp. 24)$$

where BSA (Body Surface Area) $= 0.007184 \cdot (Body\ Height)^{0.725} \cdot (Body\ Weight)^{0.425}$, and Sex: Male$=1$, Female$=-1$ $\beta$K is calculated by using the Expression 17 (Step S59). By using the acquired $\beta$K, esCO is calculated from the Expression 16 (Step S60). If the determination in Step S54 is YES, likewise, calculation of acquiring esCO from the Expression 16 is carried out (Step S60). The esCO acquired in the calculation is displayed (Step S61).

The above procedure is repeated as required.

Figure 3:
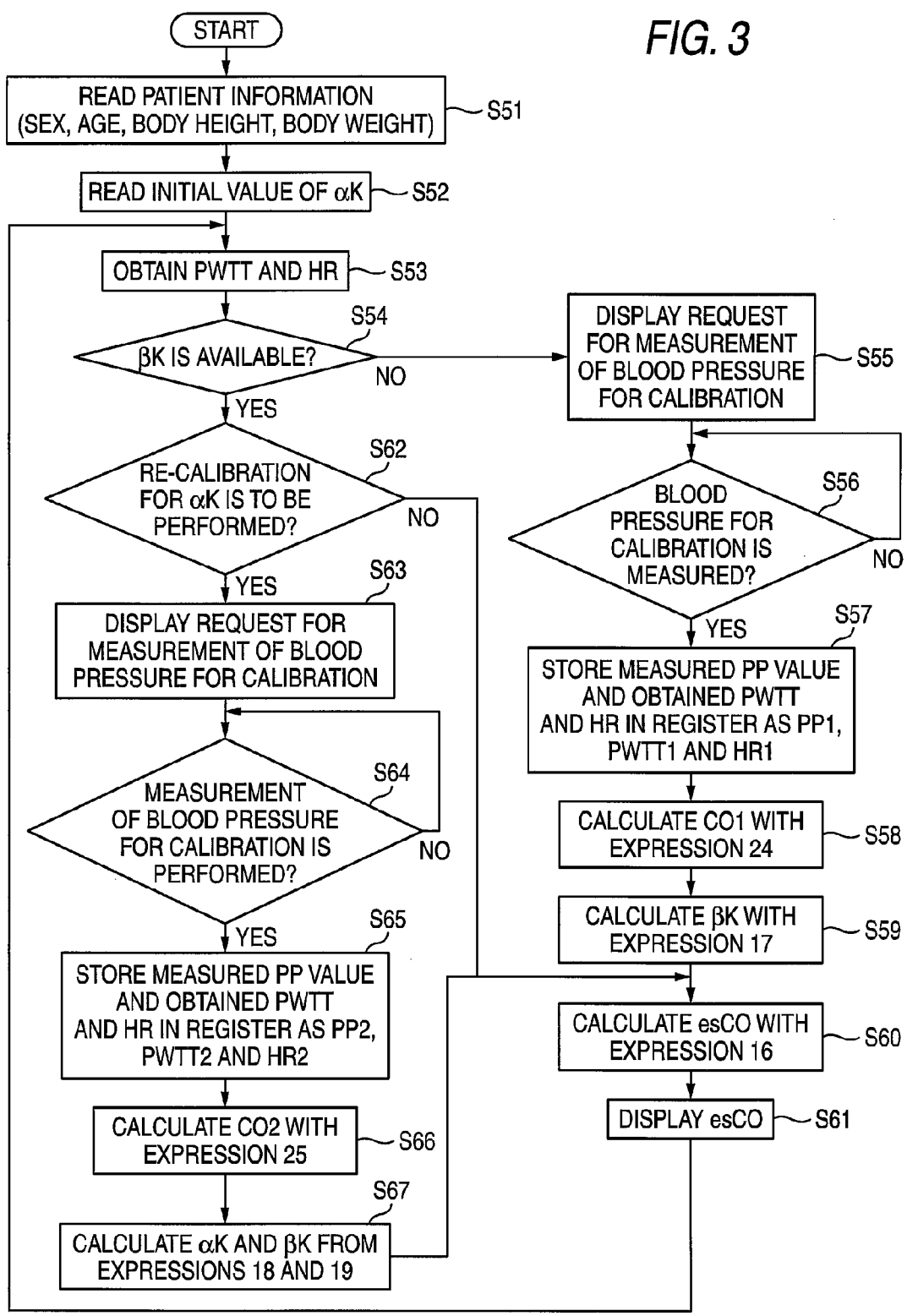
FIG. 3 is a flowchart showing a procedure in the invention in which $\alpha K$ and $\beta K$ are calibrated, and esCO is calculated.

Next, the procedure in which $\alpha$K and $\beta$K are acquired by calibration and then esCO is calculated will be described with reference to FIG. 3.

Reading of specific information (sex, age, body height, and body weight) of a patient is carried out (Step S51). Reading of the default value of $\alpha$K is carried out (Step S52). PWTT and HR are acquired (Step S53). Next, it is determined whether $\beta$K is available or not (Step S54). If the determination in Step S54 is NO, then a request for measurement of blood pressure for calibration is displayed (Step S55). It is determined whether measurement of the blood pressure for calibration has been conducted or not (Step S56). If the determination in Step S56 is YES, the measured value of the blood pressure PP, and PWTT and HR which are acquired in Step S53 are stored in the register as PP1, PWTT1, and HR1, respectively (Step S57). CO1 is calculated by using the Expression 24 (Step S58). βK is calculated by using the Expression 17 (Step S59). By using the acquired βK, esCO is calculated from the Expression 16 (Step S60). If the determination in Step S54 is YES, likewise, calculation of acquiring esCO from the Expression 16 is carried out (Step S60). The esCO acquired in the calculation is displayed (Step S61). If the determination in Step S54 is YES, it is determined whether re-calibration for αK should be carried out or not (Step S62). If the determination in Step S62 is NO, calculation of acquiring esCO from the Expression 16 is carried out in the same manner as described above (Step S60). If the determination in Step S62 is YES, then a request for measurement of blood pressure for calibration is displayed (Step S63). It is determined whether measurement of the blood pressure for calibration has been conducted or not (Step S64). If the determination in Step S64 is YES, the measured value of the blood pressure (PP), and PWTT and HR which are acquired in Step S53 are stored in the register as PP2, PWTT2, and HR2, respectively (Step S65). CO2 is calculated by using following Expression 25 (Step S66).

$$CO2 = a + b \cdot Sex + c \cdot Age + d \cdot BSA + e \cdot PWTT2 + f \cdot HR2 \cdot PP2 \quad \text{(Exp. 25)}$$

where BSA (Body Surface Area)=0.007184·(Body Height)$^{0.725}$·(Body Weight)$^{0.425}$, and Sex: Male=1, Female=−1

αK and βK are calculated from the Expressions 18 and 19 (Step S67).

Calculation of acquiring esCO from the Expression 16 is carried out by using the acquired αK and βK (Step S60). If the determination in Step S62 is NO, calculation of acquiring esCO from the Expression 16 is carried out in the same manner as described above (Step S60). The esCO acquired in the calculation is displayed (Step S61).

The above procedure is repeated as required.

Figure 4:
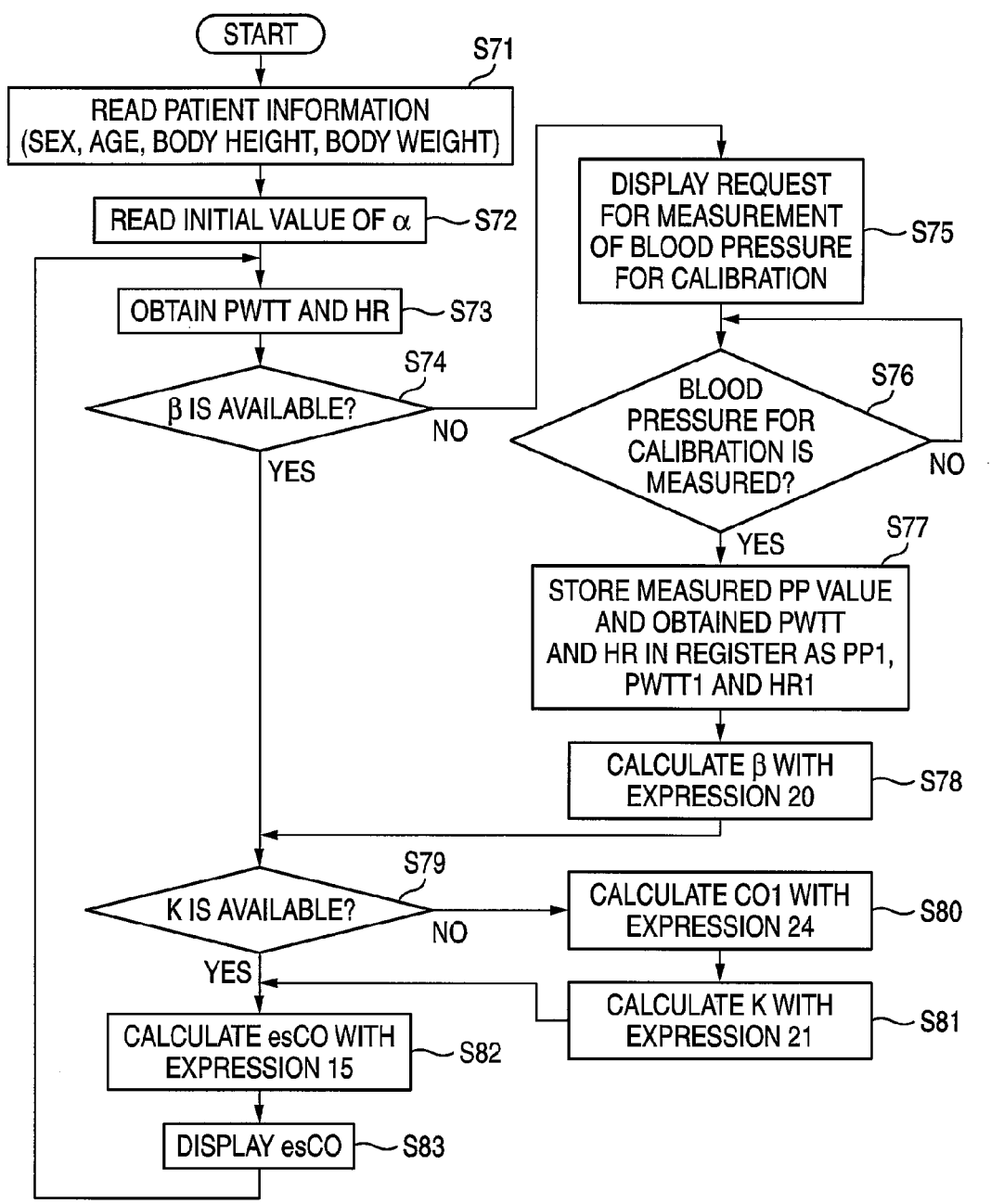
FIG. 4 is a flowchart showing a procedure in the invention in which a default value of $\alpha$ is used, $\beta$ and K are calibrated, and esCO is calculated.

Then, the procedure in which α is the default value, β and K are acquired by calibration, and then esCO is calculated will be described with reference to FIG. 4. The calibration of β is carried out when the pulse pressure is not augmented by administration of a vasoconstrictor or the like.

Reading of specific information (sex, age, body height, and body weight) of a patient is carried out (Step S71). Reading of the default value of α is carried out (Step S72). PWTT and HR are acquired (Step S73). Next, it is determined whether β is available or not (Step S74). If the determination in Step S74 is NO, then a request for measurement of blood pressure for calibration is displayed (Step S75). It is determined whether measurement of the blood pressure for calibration has been conducted or not (Step S76). If the determination in Step S76 is YES, the measured value of the blood pressure PP, and acquired PWTT and HR are stored in the register as PP1, PWTT1, and HR1, respectively (Step S77). β is calculated from the Expression 20 (Step S78). If the determination in Step S74 is YES, or after β is calculated in Step S78, it is determined whether K is available or not (Step S79). If the determination in Step S79 is NO, CO1 is calculated by using the Expression 24 (Step S80). K is calculated from the Expression 21 (Step S81). If the determination in Step S79 is YES, or after the process of Step S81 is performed, esCO is calculated from the Expression 15 (Step S82). The esCO acquired in the calculation is displayed (Step S83).

Following expression related to the esCO can be obtained from the Expressions 15, 20, 21 and 24.

$$esCO = HR \cdot (a + b \cdot Sex + c \cdot Age + d \cdot BSA + e \cdot PWTT1 + f \cdot HR1 \cdot PP1)(\alpha \cdot PWTT + \beta)/PP1 \cdot HR1$$

The above expression includes PWTT1, however, PWTT1 may be removed from the expression. In such a case, following expression can be obtained.

$$esCO = HR \cdot (a + b \cdot Sex + c \cdot Age + d \cdot BSA + f \cdot HR1 \cdot PP1)(\alpha \cdot PWTT + \beta)/PP1 \cdot HR1$$

The above expressions may be used in Step S82.

The above procedure is repeated as required.

Figure 5:
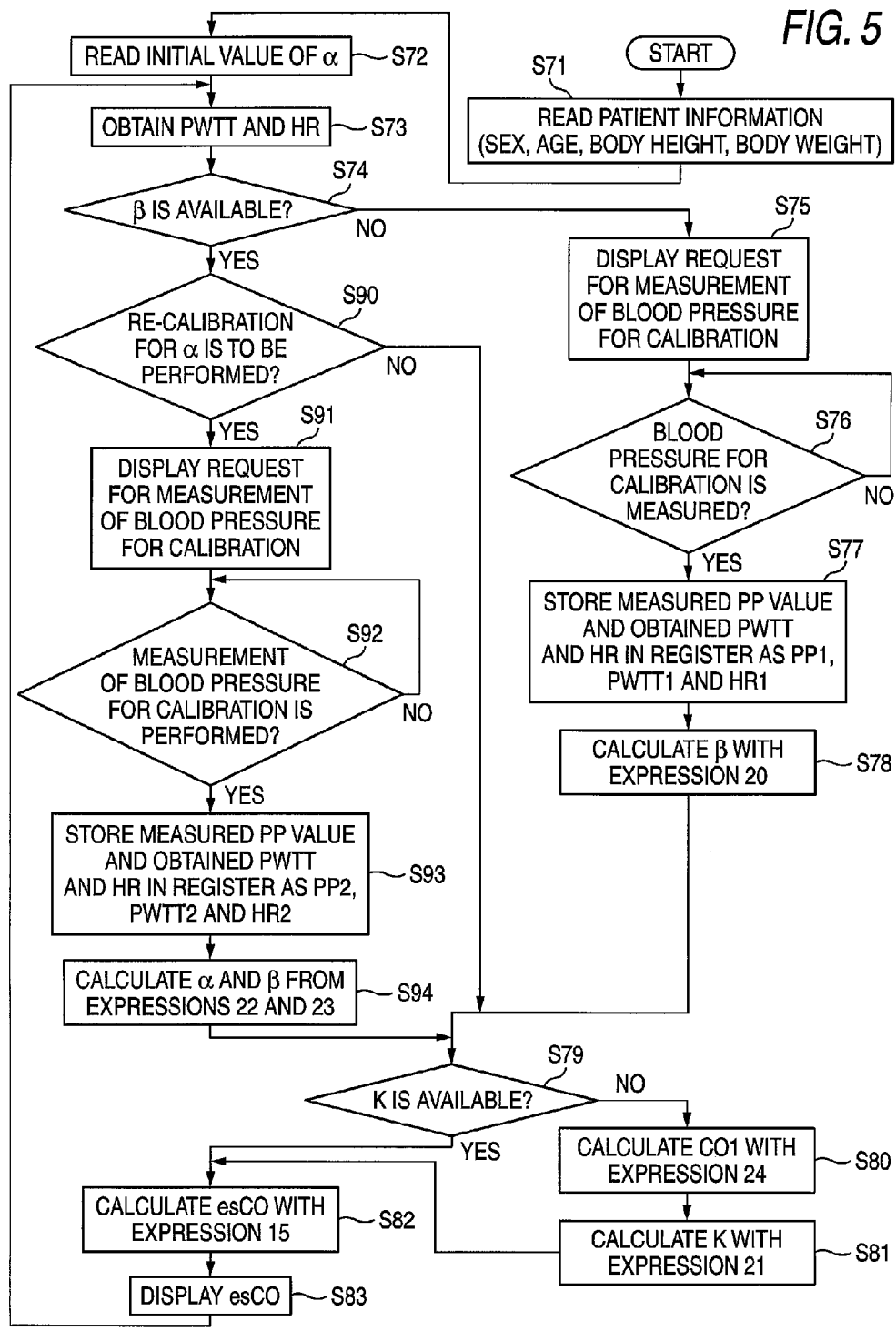
FIG. 5 is a flowchart showing a procedure in the invention in which K, $\alpha$, and $\beta$ are calibrated, and esCO is calculated.
Figure 6:
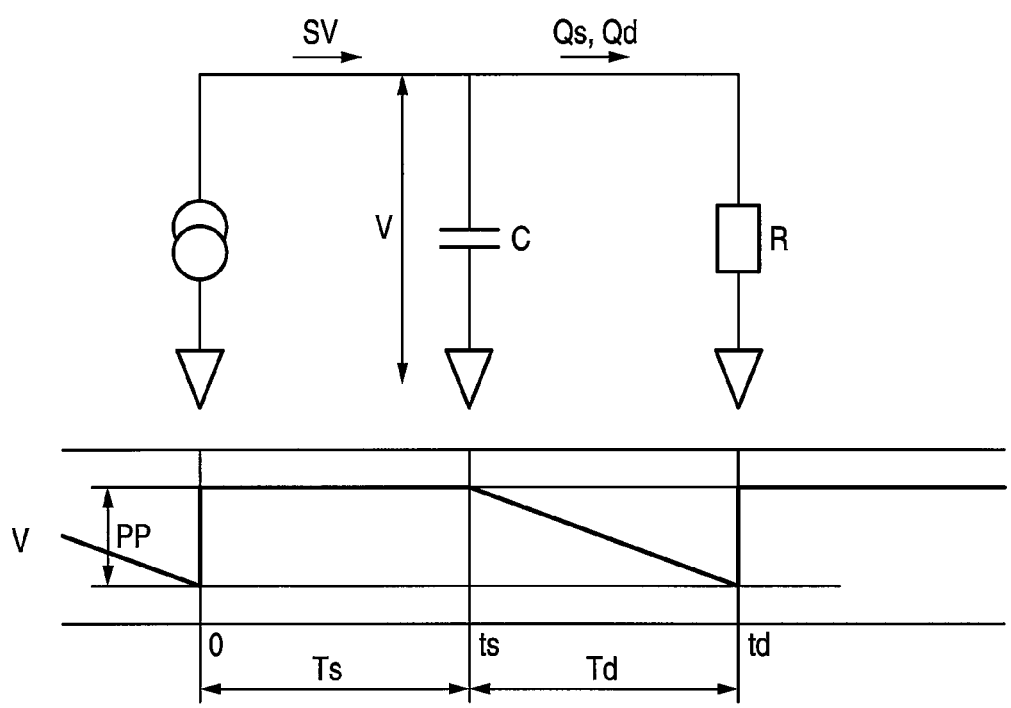
FIG. 6 is a diagram showing a Windkessel model.
Figure 7:
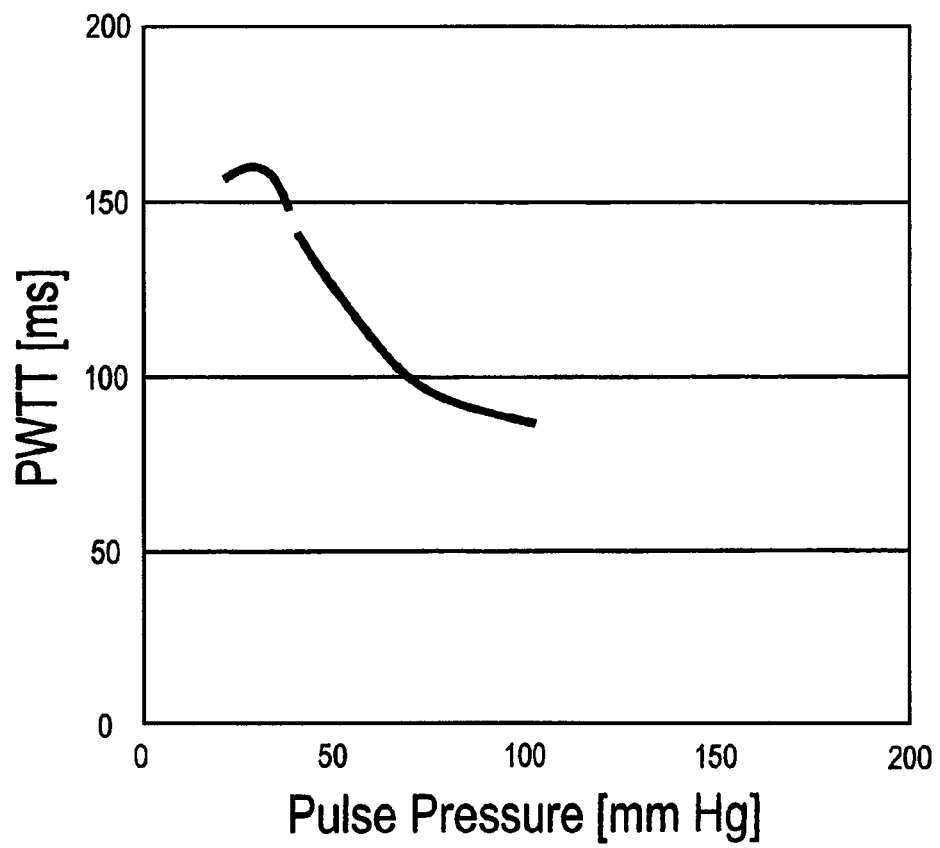
FIG. 7 is a view showing a representative relationship between PWTT and a pulse pressure PP.
Figure 8:
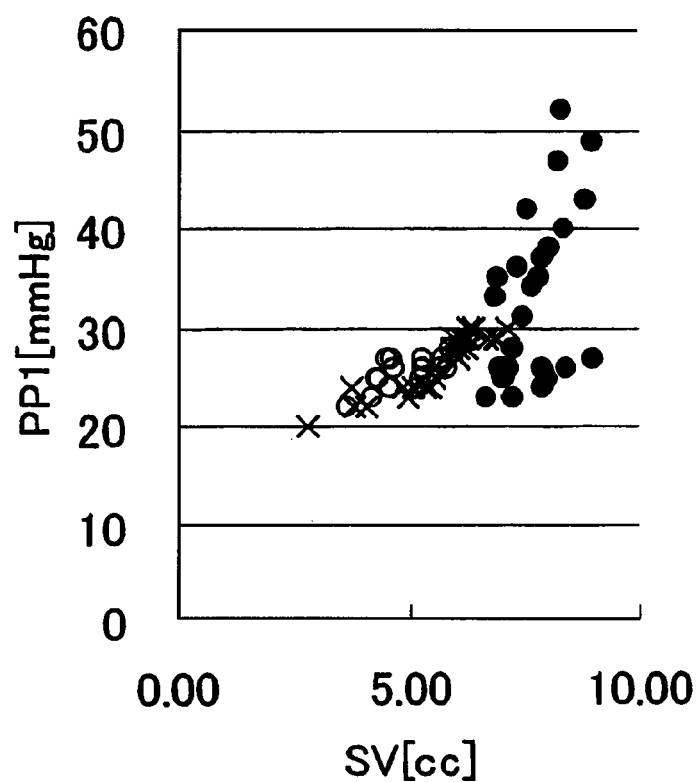
FIG. 8 is a view showing relationships between SV and PP1 measured in cases of vasoconstriction, blood removal, and cardiac suppression in an animal test.
Figure 9:
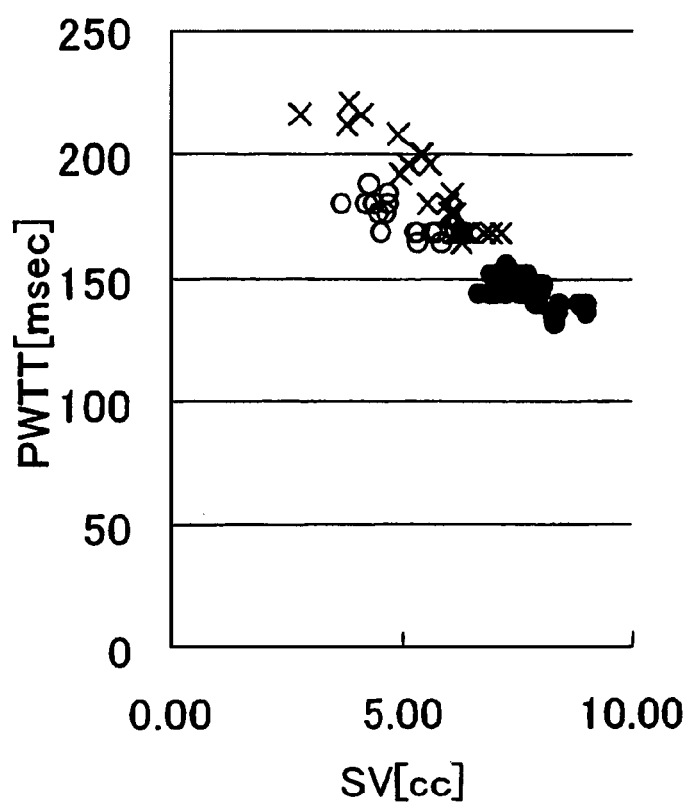
FIG. 9 is a view showing relationships between SV and PWTT measured in cases of vasoconstriction, blood removal, and cardiac suppression in an animal test.
Figure 10:
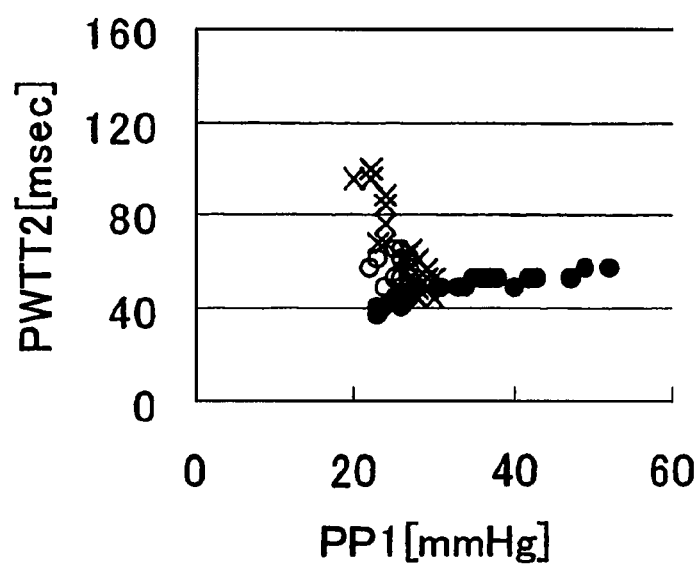
FIG. 10 is a view showing relationships between PP1 and PWTT2 measured in cases of vasoconstriction, blood removal, and cardiac suppression in an animal test.
Figure 11:
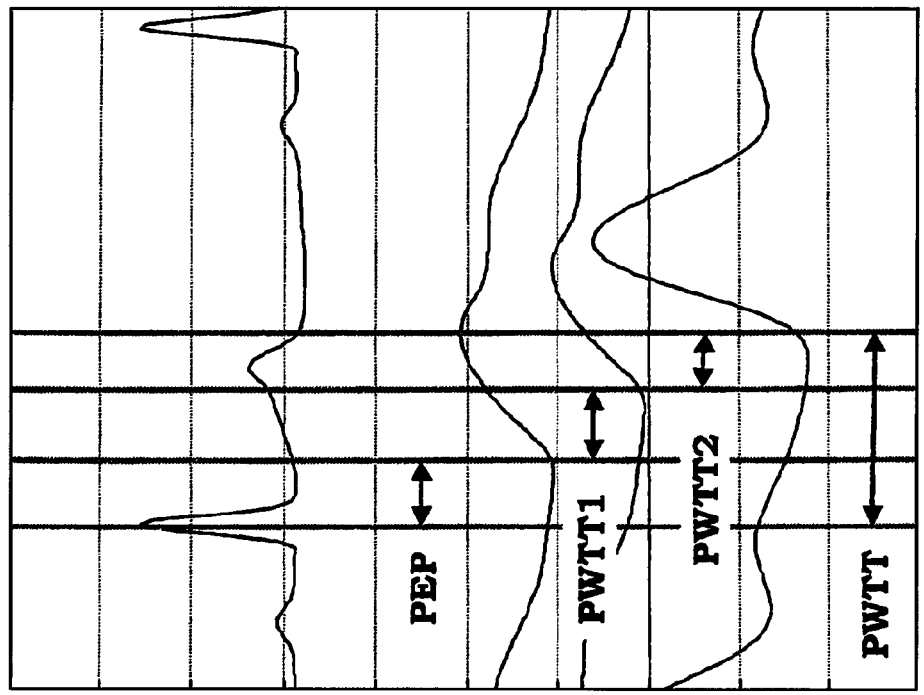
FIG. 11 is a view showing relationships among PEP, PWTT1, PWTT2, and PWTT.
Figure 12:
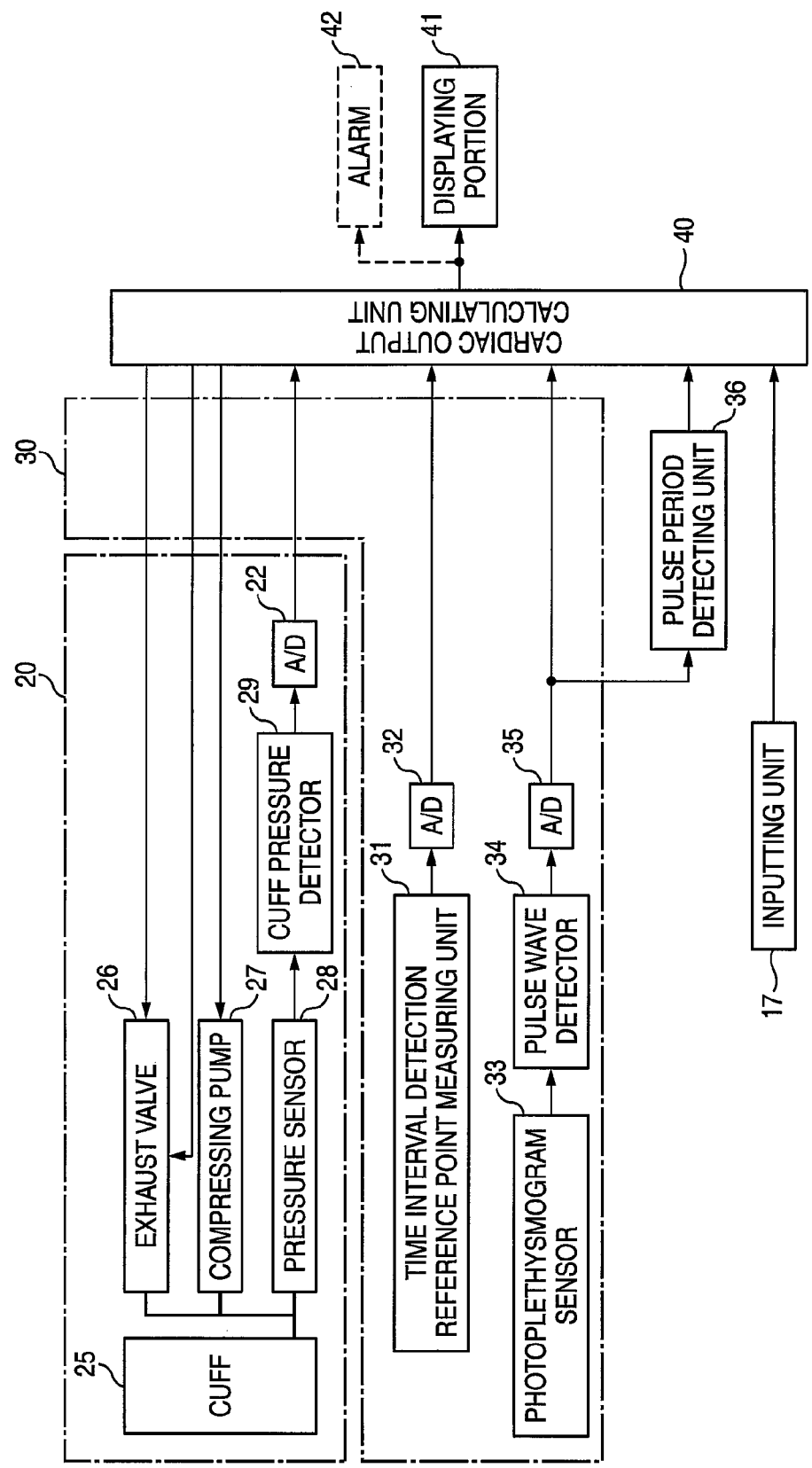
FIG. 12 is a block diagram illustrating the configuration of a conventional biological signal monitoring apparatus.
Figure 13:
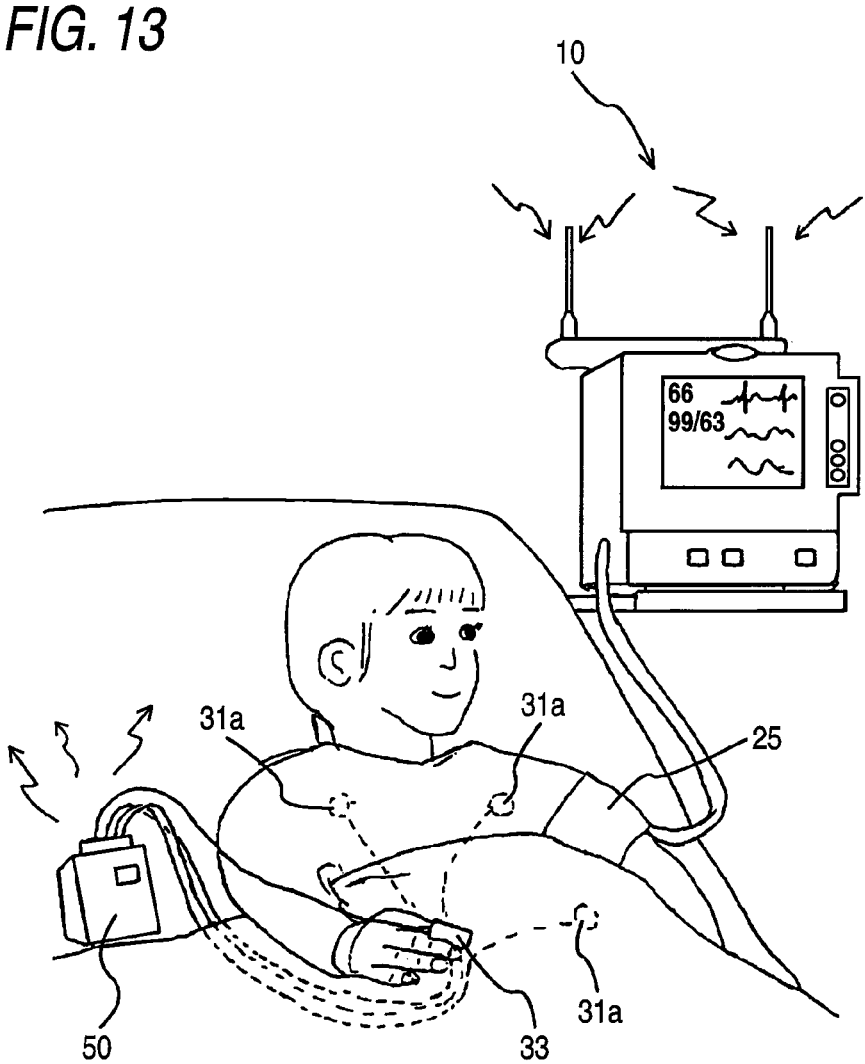
FIG. 13 is a view showing an example of a state in which an electrocardiogram measuring unit and a peripheral-pulse wave detecting unit are attached to the patient.
Figure 14:
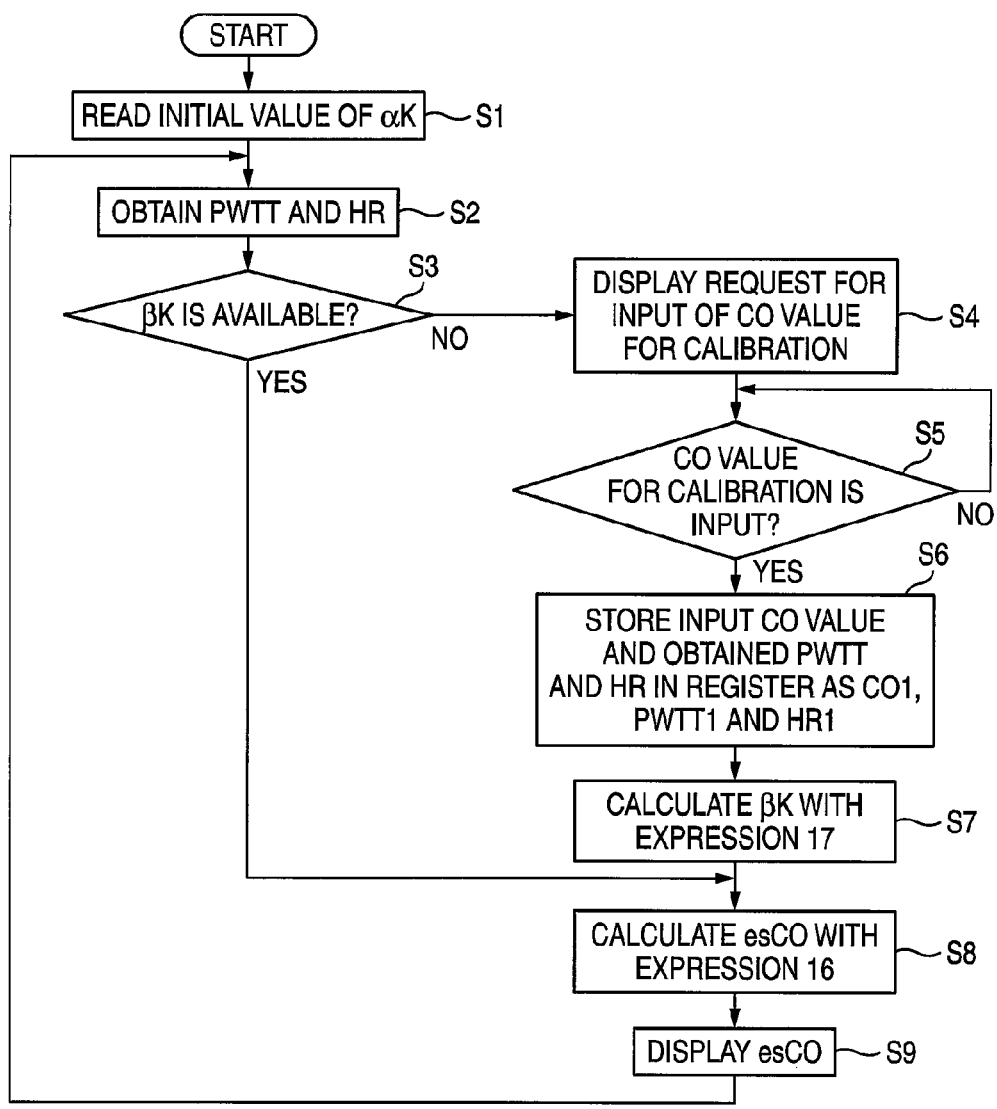
FIG. 14 is a flowchart showing a procedure in a conventional art in which a default value of $\alpha K$ is used, $\beta K$ is calibrated, and esCO is calculated.
Figure 15:
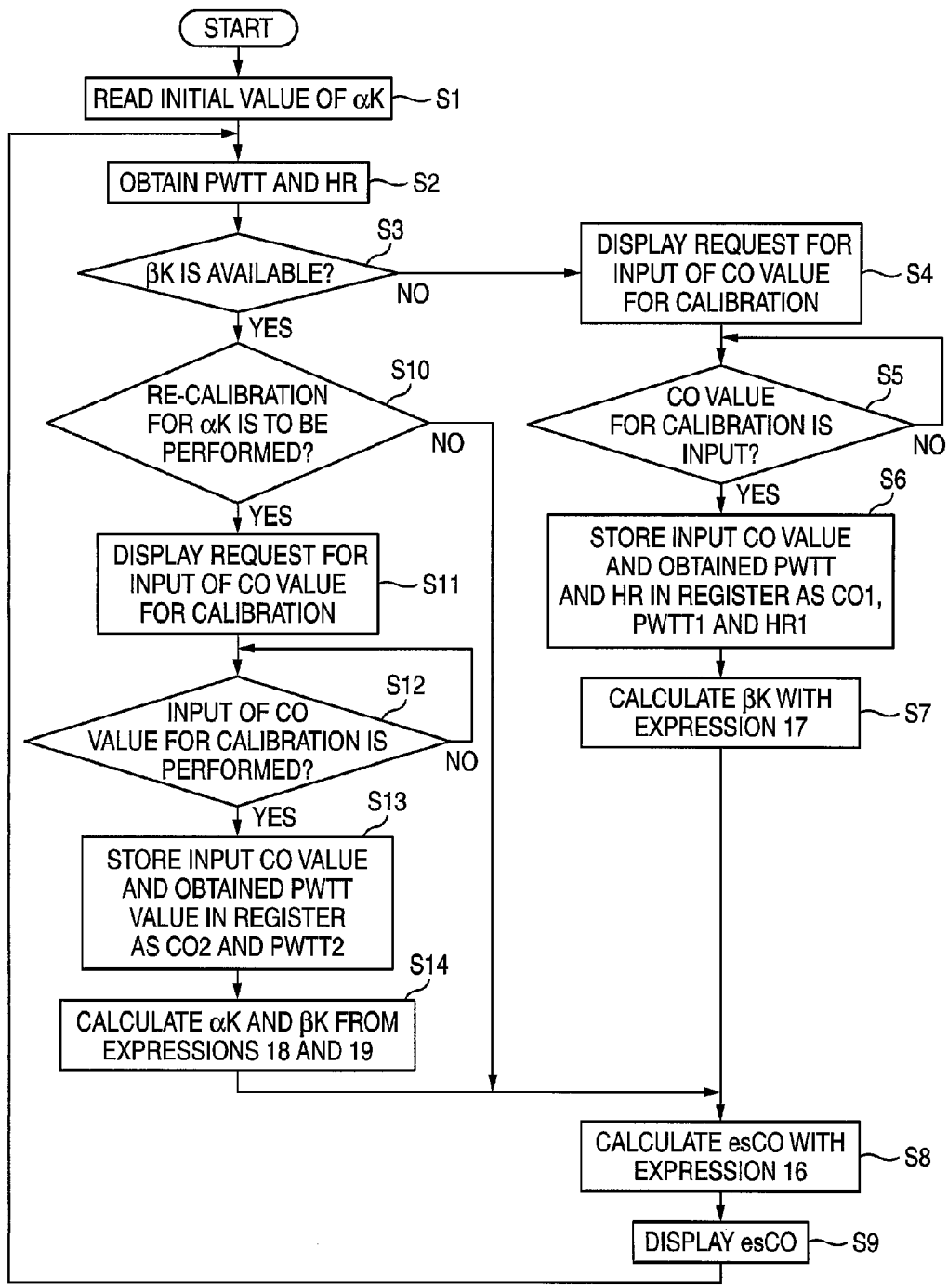
FIG. 15 is a flowchart showing a procedure in a conventional art in which $\alpha K$ and $\beta K$ are calibrated, and esCO is calculated.
Figure 16:
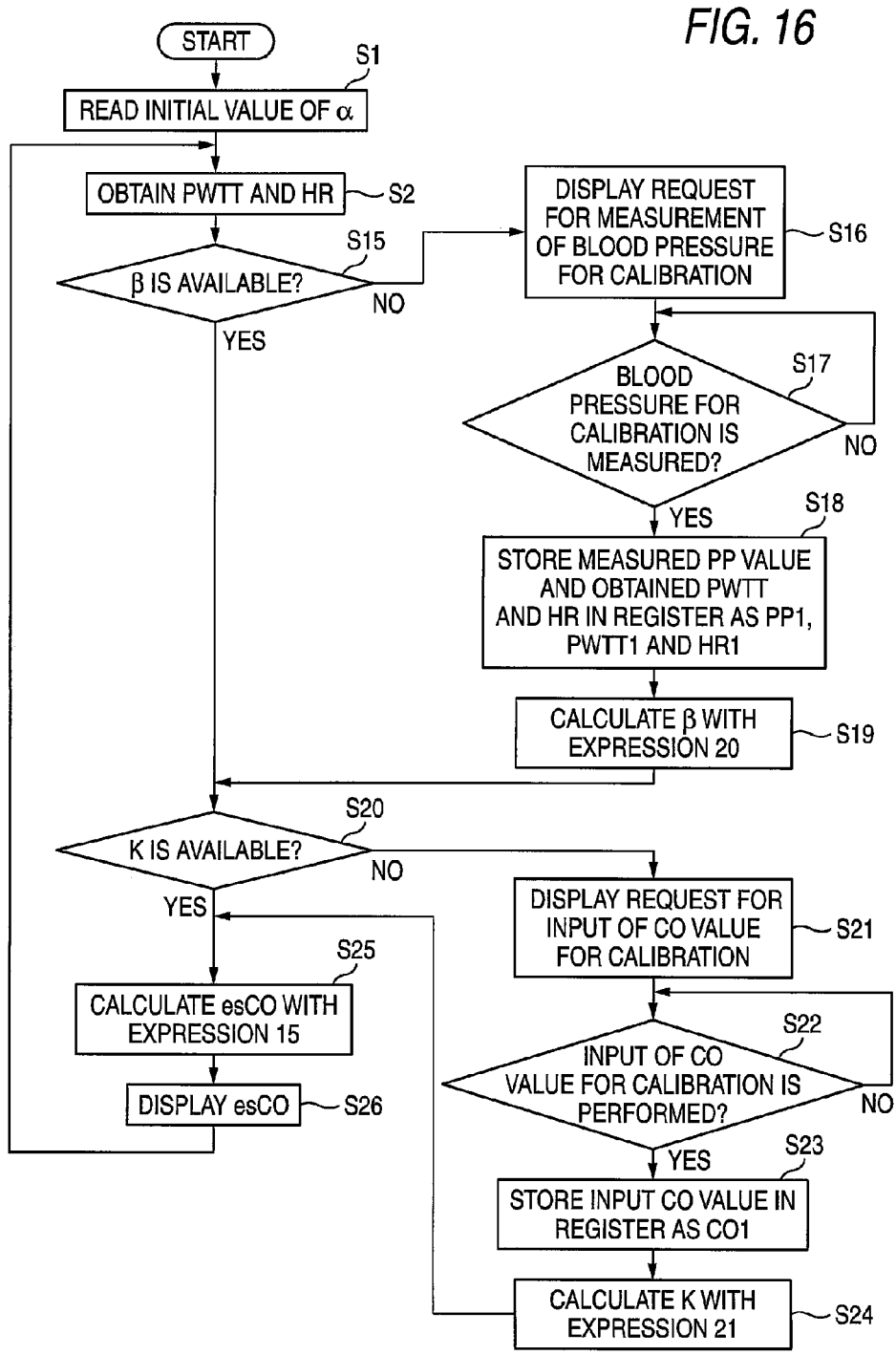
FIG. 16 is a flowchart showing a procedure in a conventional art in which a default value of $\alpha$ is used, $\beta$ and K are calibrated, and esCO is calculated.
Figure 17:
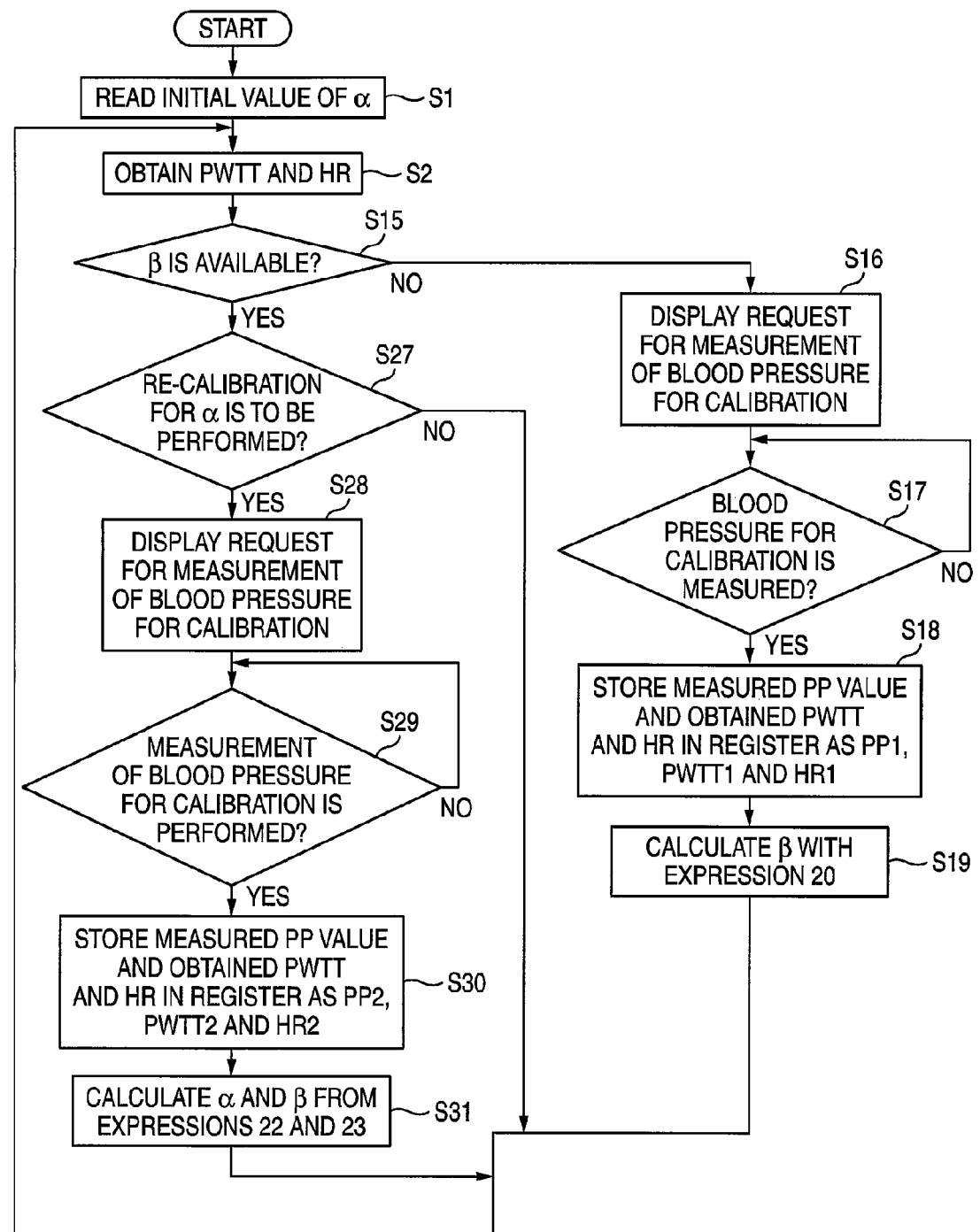
FIG. 17 is a flowchart showing a procedure in a conventional art in which K, $\alpha$, and $\beta$ are calibrated, and esCO is calculated.

Then, the procedure in which α, β, and K are acquired by calibration, and then esCO is calculated will be described with reference to FIG. 5. The calibration of α and β is carried out when the pulse pressure is not augmented by administration of a vasoconstrictor or the like.

Reading of specific information (sex, age, body height, and body weight) of a patient is carried out (Step S71). Reading of the default value of α is carried out (Step S72). PWTT and HR are acquired (Step S73). Next, it is determined whether β is available or not (Step S74). If the determination in Step S74 is NO, then a request for measurement of blood pressure for calibration is displayed (Step S75). It is determined whether measurement of the blood pressure for calibration has been conducted or not (Step S76). If the determination in Step S76 is YES, the measured value of the blood pressure PP, and acquired PWTT and HR are stored in the register as PP1, PWTT1, and HR1, respectively (Step S77). β is calculated from the Expression 20 (Step S78). If the determination in Step S74 is YES, or after β is calculated in Step S78, it is determined whether K is available or not (Step S79). If the determination in Step S79 is NO, CO1 is calculated by using the Expression 24 (Step S80). K is calculated from the Expression 21 (Step S81). If the determination in Step S79 is YES, or after the process of step S81 is performed, esCO is calculated from the Expression 15 (Step S82). The esCO acquired in the calculation is displayed (Step S83).

The above procedure is repeated as required.

If the determination in Step S74 is YES, it is determined whether re-calibration for α should be carried out or not (Step S90). If the determination in Step S90 is YES, then a request for measurement of blood pressure for calibration is displayed (Step S91). It is determined whether measurement of the blood pressure for calibration has been conducted or not (Step S92). If the determination in Step S92 is YES, the measured value of PP, and acquired PWTT and HR are stored in the register as PP2, PWTT2, and HR2, respectively (Step S93). α and β are calculated from the Expressions 22 and 23 (Step S94). If the determination in Step S90 is NO, it is determined whether K is available or not (Step S79).

Alternatively, the measurement of blood pressure for calibration may not be performed, and a blood pressure value which is measured by another sphygmomanometer may be key-input. Furthermore, the peripheral pulse wave may include also that indicative of a volumetric change in addition to the SpO2 pulse wave.

According to an aspect of the invention, as shown in the above-described flowcharts of FIGS. 2 to 5, a calibrating process in which the CO value for calibration is input is not required, and therefore monitoring can be performed in an easy and continuous manner.

What is claimed is:

1. A method of measuring a blood volume, the method comprising:
   reading individual specific information of a patient related to oxygen metabolism;
   calculating an input cardiac output value based on the read individual specific information of the patient;
   calculating K based on the calculated input cardiac output;

acquiring by a biological signal monitoring apparatus a pulse wave propagation time (PWTT), a heart rate (HR) of the patient, and coefficients ($\alpha$ and $\beta$) inherent to the patient; and calculating a cardiac output by using an expression of $esCO=K\cdot(\alpha\cdot PWTT+\beta)\cdot HR$, where esCO is the cardiac output, wherein the input cardiac output value is calculated by using an expression of $$CO=a+b\cdot Sex+c\cdot Age+d\cdot BSA+e\cdot PWTT+f\cdot HR\cdot PP$$

where CO is the input cardiac output value;

Sex is the sexuality of the patient, when the patient is male, Sex=1, and when the patient is female, Sex=−1;

Age is the age of the patient;

BSA is the body surface area of the patient;

PWTT is the pulse wave propagation time;

HR is the heart rate of the patient;

PP is a pulse pressure of the patient; and a, b, c, d, e, and f are coefficients inherent to the patient.

2. The method according to claim 1, further comprising, acquiring constants for each of the individual specific information by multiple linear regression analysis.

3. A method of measuring a blood volume, the method comprising:

reading individual specific information of a patient related to oxygen metabolism;

calculating an input cardiac output value based on the read individual specific information of the patient;

acquiring by a biological signal monitoring apparatus a pulse wave propagation time (PWTT), a heart rate (HR) of the patient, sexuality of the patient (Sex), an age of the patient (Age); a body surface area (BSA) of the patient, a heart rate input ($HR_0$) at a timing of calibration; a pulse pressure input ($PP_0$) at the timing of calibration, coefficients ($\alpha$ and $\beta$) inherent to the patient and constants (a1, b1, c1, d1, and e1); and calculating a cardiac output by using an expression of $$esCO=HR\cdot(a1+b1\cdot Sex+c1\cdot Age+d1\cdot BSA+e1\cdot HR_0\cdot PP_0)(\alpha\cdot PWTT+\beta)/PP_0\cdot HR_0$$

where esCO is the cardiac output.

4. The method according to claim 3 further comprising, acquiring the constants a1, b1, c1, d1, and e1 by multiple linear regression analysis from individual specific information and actual CO values of a plurality of subjects.

5. A method of measuring a blood volume, the method comprising:

reading individual specific information of a patient related to oxygen metabolism;

calculating an input cardiac output value based on the read individual specific information of the patient;

acquiring by a biological signal monitoring apparatus a pulse wave propagation time (PWTT), a heart rate (HR) of the patient, sexuality of the patient (Sex), an age of the patient (Age); a body surface area (BSA) of the patient, a heart rate input ($HR_0$) at a timing of calibration; a pulse pressure input ($PP_0$) at the timing of calibration, coefficients ($\alpha$ and $\beta$) inherent to the patient and constants (a2, b2, c2, d2, e2 and f2); and calculating a cardiac output by using an expression of $$esCO=HR\cdot(a2+b2\cdot Sex+c2\cdot Age+d2\cdot BSA+e2\cdot HR_0\cdot PP_0+f2\cdot PWTT_0)(\alpha\cdot PWTT+\beta)/PP_0\cdot HR_0$$

where esCO is the cardiac output.

6. The method according to claim 5 further comprising, acquiring the constants a2, b2, c2, d2, e2, and f2 by multiple linear regression analysis from individual specific information and actual CO values of a plurality of subjects.

7. A non-transitory computer-readable recording medium storing a computer program for a blood measuring apparatus to execute a method of measuring a blood volume, the method comprising:

reading individual specific information of a patient related to oxygen metabolism;

calculating an input cardiac output value based on the read individual specific information of the patient;

calculating K based on the calculated input cardiac output;

acquiring by a biological signal monitoring apparatus a pulse wave propagation time (PWTT), a heart rate (HR) of the patient, and coefficients ($\alpha$ and $\beta$) inherent to the patient; and calculating a cardiac output by using an expression of $esCO=K\cdot(\alpha\cdot PWTT+\beta)\cdot HR$, where esCO is the cardiac output, wherein the input cardiac output value is calculated by using an expression of $$CO=a+b\cdot Sex+c\cdot Age+d\cdot BSA+e\cdot PWTT+f\cdot HR\cdot PP$$

where CO is the input cardiac output value;

Sex is the sexuality of the patient, when the patient is male, Sex=1, and when the patient is female, Sex=−1;

Age is the age of the patient;

BSA is the body surface area of the patient;

PWTT is the pulse wave propagation time;

HR is the heart rate of the patient;

PP is a pulse pressure of the patient; and a, b, c, d, e, and f are coefficients inherent to the patient.

8. An apparatus for measuring a blood volume, the apparatus comprising:

a first receiver configured to receive an input of individual specific information of a patient; and a controlling unit which is configured to receive the input of the individual specific information of the patient related to oxygen metabolism from the first receiver, calculate an input cardiac output value based on the read individual specific information of the patient, calculate K based on the calculated input cardiac output, acquire a pulse wave propagation time (PWTT), a heart rate (HR) of the patient, and coefficients ($\alpha$ and $\beta$) inherent to the patient and calculate a cardiac output by using an expression of $esCO=K\cdot(\alpha\cdot PWTT+\beta)\cdot HR$, where esCO is the cardiac output, wherein the input cardiac output value is calculated by using an expression of $$CO=a+b\cdot Sex+c\cdot Age+d\cdot BSA+e\cdot PWTT+f\cdot HR\cdot PP$$

where CO is the input cardiac output value;

Sex is the sexuality of the patient, when the patient is male, Sex=1, and when the patient is female, Sex=−1;

Age is the age of the patient;

BSA is the body surface area of the patient;

PWTT is the pulse wave propagation time;

HR is the heart rate of the patient;

PP is a pulse pressure of the patient; and a, b, c, d, e, and f are coefficients inherent to the patient.

9. The apparatus according to claim 8, further comprising:

a second receiver configured to receive a timing of calibration and the second receiver configured to send the timing of calibration to the controlling unit.

10. The apparatus according to claim 8, further comprising:

a time interval detection reference point measuring unit;
a pulse wave detecting unit;
a heart rate calculating unit which calculate the heart rate based on output from the time interval detection reference point measuring unit or the pulse wave detecting unit;
an inputting unit through which at least an age, sexuality, and BSA of the patient are input; and
a blood pressure inputting or blood pressure measuring unit, wherein
the controlling unit receives information from the time interval detection reference point measuring unit, the pulse wave detecting unit, the heart rate calculating unit, the inputting unit and the blood pressure inputting or blood pressure measuring unit.

11. The apparatus according to claim 10, wherein the time interval detection reference point measuring unit is an electrocardiogram measuring unit.

* * * * *